(12) United States Patent
Endo

(10) Patent No.: US 11,132,795 B2
(45) Date of Patent: Sep. 28, 2021

(54) MEDICAL IMAGE PROCESSING APPARATUS

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/857,163

(22) Filed: Apr. 23, 2020

(65) Prior Publication Data

US 2020/0258224 A1 Aug. 13, 2020

Related U.S. Application Data

(63) Continuation of application No. PCT/JP2018/038511, filed on Oct. 16, 2018.

(30) Foreign Application Priority Data

Oct. 26, 2017 (JP) .............................. JP2017-207132

(51) Int. Cl.
*G06T 7/00* (2017.01)
*A61B 5/02* (2006.01)
*A61B 5/1455* (2006.01)

(52) U.S. Cl.
CPC ........ *G06T 7/0012* (2013.01); *A61B 5/02042* (2013.01); *A61B 5/14551* (2013.01)

(58) Field of Classification Search
CPC ... A61B 5/00; A61B 5/02042; A61B 5/14551; G06T 7/0012
See application file for complete search history.

(56) References Cited

U.S. PATENT DOCUMENTS

| 8,918,740 | B2 | 12/2014 | Nishiyama | |
|---|---|---|---|---|
| 10,653,295 | B2 | 5/2020 | Ebata | |
| 2002/0057826 | A1* | 5/2002 | Imamura | G06T 7/0012 382/128 |
| 2004/0081343 | A1* | 4/2004 | Takeo | G06T 7/0012 382/131 |

(Continued)

FOREIGN PATENT DOCUMENTS

| EP | 2601880 | 6/2013 |
|---|---|---|
| JP | 2013085593 | 5/2013 |

(Continued)

OTHER PUBLICATIONS

"Search Report of Europe Counterpart Application", dated Oct. 29, 2020, p. 1-p. 8.

(Continued)

*Primary Examiner* — John J Lee
(74) *Attorney, Agent, or Firm* — JCIPRNET

(57) ABSTRACT

A medical image processing apparatus includes: a medical image acquisition unit that acquires a medical image including a subject image; a display unit that displays a plurality of the medical images; an abnormal region determination unit that determines an abnormal region by using the medical images; a malignancy discrimination unit that discriminates a degree of malignancy of an abnormality included in the abnormal region; and a display control unit that emphasizes or suppresses display of at least some medical images among the plurality of medical images by using the degree of malignancy, in displaying the plurality of medical images on the display unit.

11 Claims, 10 Drawing Sheets

(56) References Cited

U.S. PATENT DOCUMENTS

2011/0144482 A1* 6/2011 Sendai .................. G06T 7/0012
600/425

FOREIGN PATENT DOCUMENTS

| WO | 2012132840 | 10/2012 |
| WO | 2017057574 | 4/2017 |

OTHER PUBLICATIONS

"International Search Report (Form PCT/ISA/210)" of PCT/JP2018/038511, dated Jan. 15, 2019, with English translation thereof, pp. 1-3.
"Written Opinion of the International Searching Authority (Form PCT/ISA/237)" of PCT/JP2018/038511, dated Jan. 15, 2019, with English translation thereof, pp. 1-8.

* cited by examiner

MEDICAL IMAGE PROCESSING APPARATUS

CROSS-REFERENCE TO RELATED APPLICATIONS

This application is a Continuation of PCT International Application No. PCT/JP2018/038511 filed on 16 Oct. 2018, which claims priority under 35 U.S.C § 119(a) to Japanese Patent Application No. 2017-207132 filed on 26 Oct. 2017. The above application is hereby expressly incorporated by reference, in its entirety, into the present application.

BACKGROUND OF THE INVENTION

1. Field of the Invention

The present invention relates to a medical image processing apparatus that displays a plurality of medical images.

2. Description of the Related Art

In the related art, an apparatus that acquires an image including a subject image (hereinafter, referred to as a medical image) among apparatuses relevant to medical care (hereinafter, referred to as a medical apparatus) presents the acquired medical image to a doctor. Then, the doctor performs diagnosis or the like using the medical image obtained from the medical apparatus as one of determination materials.

Many medical apparatuses acquire a plurality of medical images in one examination, depending on the specific examination content and the like. For this reason, a medical apparatus, an apparatus for displaying medical images acquired by the medical apparatus, or the like arranges the plurality of acquired medical images and presents a display list of the medical images, thereby facilitating selection of images used for diagnosis or the like. In addition, in a case where the number of medical images to be acquired and displayed is particularly large, and the like, it may be difficult to quickly and appropriately select the medical images to be used for diagnosis or the like even in a case where the display list of the medical images is presented. For this reason, in some cases, a medical apparatus that presents a display list of a plurality of medical images is devised so that not only the plurality of medical images are simply displayed as a list, but also a doctor or the like can easily find or select the medical images necessary for diagnosis or the like.

For example, a capsule endoscope is a medical apparatus that acquires a large number of medical images and presents a display list of the medical images. JP2013-085593A discloses an image display apparatus for a capsule endoscope in which, in presenting a display list of endoscopic images that are a plurality of medical images, priority is determined for the plurality of medical images, and the medical images are arranged in order of the priority and are presented as a display list.

SUMMARY OF THE INVENTION

The image display apparatus disclosed in JP2013-085593A determines the priority for a display list of the medical images based on red color (redness), red density, a red area, or combination thereof. This is for discriminating the presence and degree of bleeding. However, although the presence and degree of bleeding is one of useful diagnostic materials, in a case where the priority for a display list of the medical images is determined based on only the presence and degree of bleeding, for example, a lesion without bleeding may be overlooked in some cases. In addition, for example, in a case of acquiring a medical image with a different color scheme from a normal image, such as a so-called special light image, in a case where the priority of such a medical image is evaluated as low, as a result, even in a case where a serious lesion is included, it may be overlooked in some cases. For this reason, in a medical apparatus or the like that presents a display list of a plurality of medical images, a display list that enables a doctor or the like to more quickly and accurately select medical images necessary for diagnosis or the like is demanded.

An object of the present invention is to provide a medical image processing apparatus capable of selecting medical images necessary for diagnosis or the like more quickly and accurately than before, in presenting a display list of a plurality of medical images.

A medical image processing apparatus of the present invention comprises: a medical image acquisition unit that acquires a medical image including a subject image; a display unit that displays a plurality of the medical images; an abnormal region determination unit that determines an abnormal region by using the medical images; a malignancy discrimination unit that discriminates a degree of malignancy of an abnormality included in the abnormal region; and a display control unit that emphasizes or suppresses display of at least some medical images among the plurality of medical images by using the degree of malignancy, in displaying the plurality of medical images on the display unit.

It is preferable that the malignancy discrimination unit discriminates a type of the abnormality or a degree of progress of the abnormality included in the abnormal region, and determines the degree of malignancy by using the type of the abnormality or the degree of progress of the abnormality.

It is preferable that the medical image processing apparatus further comprises a storage unit that stores a correspondence that associates the type of the abnormality or the degree of progress of the abnormality with the degree of malignancy, and the malignancy discrimination unit obtains the degree of malignancy from the type of the abnormality or the degree of progress of the abnormality by using the correspondence stored in the storage unit.

It is preferable that the correspondence is set for each patient or for each doctor.

It is preferable that in a case where the correspondence is changed, the storage unit stores the changed correspondence.

It is preferable that the display control unit arranges the plurality of medical images in order of the degree of malignancy.

It is preferable that the display control unit emphasizes or suppresses display of at least some medical images among the plurality of medical images by adding an emphasis flag to the medical image, adding a character to the medical image, adjusting a display color of the medical image, or adjusting a display size of the medical image.

It is preferable that the medical image processing apparatus further comprises a same abnormal region determination unit that determines whether or not the plurality of medical images each have the abnormal region including the same abnormality, and in a case where there are two or more medical images each having the abnormal region including the same abnormality, the display control unit emphasizes or suppresses display of at least some medical images among the two or more medical images each having the abnormal region including the same abnormality by using the degree of malignancy and an imaging distance of the medical image.

It is preferable that the display control unit emphasizes or suppresses display of the medical image having a relatively short imaging distance, among the two or more medical images each having the abnormal region including the same abnormality.

It is preferable that the display control unit emphasizes or suppresses display of the medical image having a relatively long imaging distance, among the two or more medical images each having the abnormal region including the same abnormality.

It is preferable that the display control unit emphasizes or suppresses display of the medical image of which the imaging distance is close to a predetermined imaging distance determined for each imaging region in comparison with display of the other medical images, among the two or more medical images each having the abnormal region including the same abnormality.

It is preferable that the display control unit preferentially emphasizes display of one or the plurality of medical images of which the imaging distance is relatively close to a reference imaging distance that differs depending on a procedure or suppresses display of one or the plurality of medical images of which the imaging distance is relatively far from the reference imaging distance, among the plurality of medical images.

The medical image processing apparatus of the present invention can present a display list of medical images necessary for diagnosis or the like, which can be selected more quickly and accurately than before, in presenting a display list of a plurality of medical images.

DESCRIPTION OF THE PREFERRED EMBODIMENTS

First Embodiment

Figure 1:
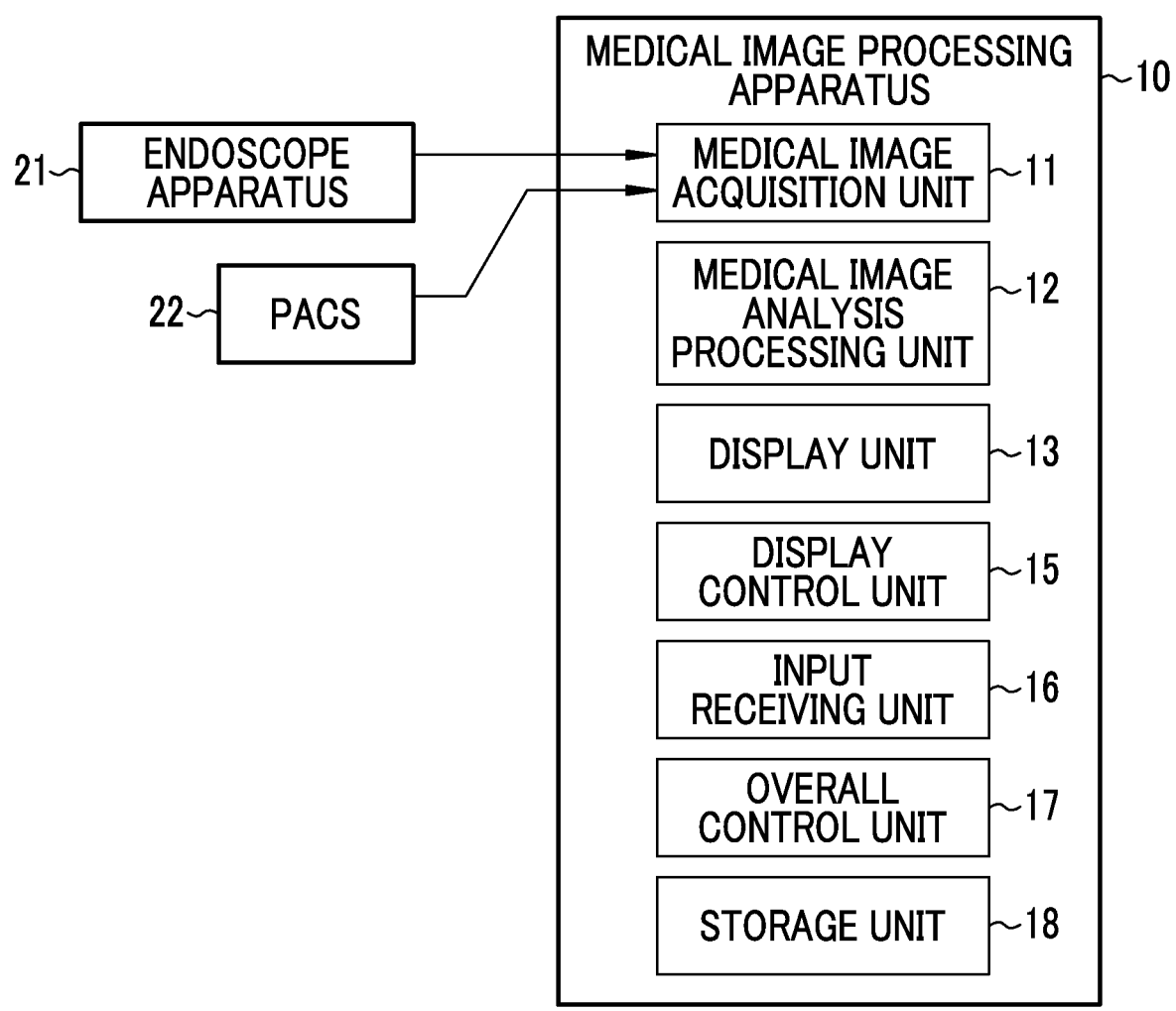
FIG. 1 is a block diagram of a medical image processing apparatus.

As shown in FIG. 1, a medical image processing apparatus 10 comprises a medical image acquisition unit 11, a medical image analysis processing unit 12, a display unit 13, a display control unit 15, an input receiving unit 16, an overall control unit 17, and a storage unit 18.

The medical image acquisition unit 11 acquires a medical image including a subject image, directly from an endoscope apparatus 21 or the like that is a medical apparatus, or through a management system such as a picture archiving and communication system (PACS) 22, or other information systems. The medical image is a still image or a motion picture (a so-called examination motion picture). In a case where the medical image is a motion picture, the medical image acquisition unit 11 can acquire a frame image forming a motion picture after examination as a still image. In addition, in a case where the medical image is a motion picture, display of the medical image includes not only displaying a still image of one representative frame forming the motion picture but also reproducing the motion picture once or multiple times. In addition, the medical image acquired by the medical image acquisition unit 11 includes an image automatically captured by a medical apparatus such as the endoscope apparatus 21 regardless of a capturing instruction of a doctor, in addition to an image captured by a doctor using a medical apparatus such as the endoscope apparatus 21.

In the case of being capable of acquiring a plurality of medical images, the medical image acquisition unit 11 can selectively acquire one or a plurality of medical images among these medical images. In addition, the medical image acquisition unit 11 can acquire a plurality of medical images acquired in a plurality of different examinations. For example, it is possible to acquire one or both of a medical image acquired in an examination performed in the past and a medical image acquired in the latest examination. That is, the medical image acquisition unit 11 acquires a medical image optionally.

In the present embodiment, the medical image processing apparatus 10 is connected to the endoscope apparatus 21 to acquire a medical image from the endoscope apparatus 21. That is, in the present embodiment, the medical image is an endoscopic image.

In addition, the medical image acquisition unit 11 can acquire one or a plurality of endoscopic images (medical images) having different imaging conditions. The imaging condition is a condition relating to imaging of a medical image, and is, for example, the spectrum of illumination light, the presence or absence or intensity of image processing at the time of generating a medical image, and the like. The spectrum of the illumination light is an intensity distribution for each wavelength, and includes the concept of a wavelength band and a center wavelength. The image processing at the time of generating a medical image is, for example, processing related to adjustment of a color or the like that emphasizes a specific tissue, structure, or lesion. In addition, the medical image acquisition unit 11 can acquire one or a plurality of endoscopic images that are not used for display on the display unit 13. The endoscopic images that are not used for display are, for example, used for an analysis process of an endoscopic image (medical image), such as detection of an abnormal region.

Figure 2:
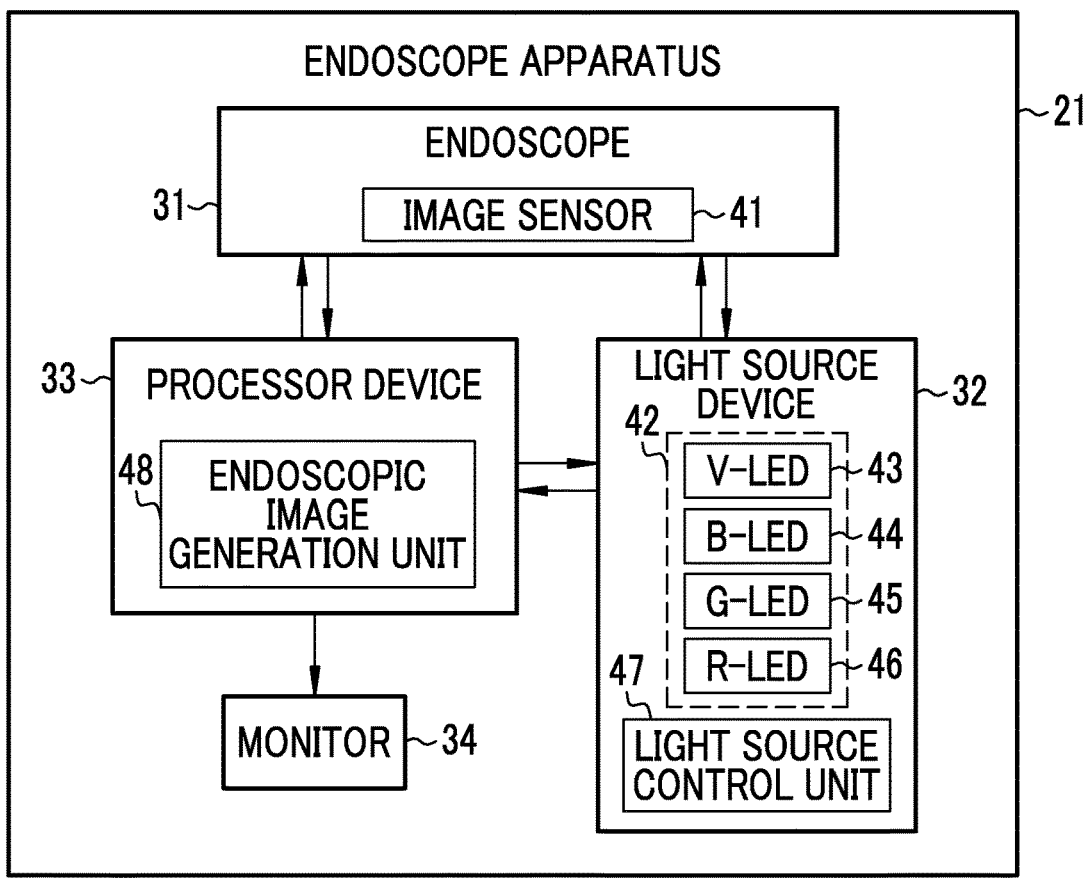
FIG. 2 is a block diagram of an endoscope apparatus.

As shown in FIG. 2, in the present embodiment, the endoscope apparatus 21 to which the medical image processing apparatus 10 is connected has an endoscope 31 that emits at least one of light in a white wavelength band or light in a specific wavelength band to image a subject, a light source device 32 that emits illumination light to the inside of the subject through the endoscope 31, a processor device 33, and a monitor 34 for displaying an endoscopic image or the like captured using the endoscope 31.

The endoscope 31 comprises an image sensor 41 that images the subject by using illumination light reflected or scattered by the subject, or fluorescence emitted by the subject or a medicine or the like administered to the subject. The image sensor 41 is, for example, a complementary metal oxide semiconductor (CMOS) color sensor (a sensor having a color filter).

The light source device 32 includes a light source unit 42 and a light source control unit 47. The light source unit 42 can emit a plurality of types of illumination light having different spectra. The light source unit 42 comprises, for example, a light emitting device such as a light emitting diode (LED), a laser diode (LD), or a xenon lamp. In addition, the light source unit 42 comprises a prism, a mirror, an optical fiber, an optical filter for adjusting a wavelength band or a light amount, and the like, as necessary. In the present embodiment, the light source unit 42 comprises a V-LED 43 that emits violet light having a center wavelength of about 405 nm, a B-LED 44 that emits blue light having a center wavelength of about 450 nm, a G-LED 45 that emits green light having a center wavelength of about 540 nm, and an R-LED 46 that emits red light having a center wavelength of about 630 nm.

The light source control unit 47 controls a light emitting source included in the light source unit 42, and generates illumination light to be used by the endoscope 31 to image a subject. In a case where the light source unit 42 includes a plurality of light emitting devices, the light source control unit 47 can individually control the light emission timing and the light emission amount of each light emitting device. Therefore, the light source device 32 can supply the plurality of types of illumination light having different spectra to the endoscope 31 at any timing and any intensity. For example, in the present embodiment, the light source device 32 can emit violet light, blue light, green light, red light, or light obtained by mixing two or more of these colors at any intensity ratio in addition to white light under the control performed by the light source control unit 47, as illumination light at any timing and any intensity. In addition, the light source device 32 can emit light having a specific narrow wavelength band (a so-called narrow-band light) as illumination light due to characteristics of a light emitting device or use of an optical filter. For example, light in a shorter wavelength band than the green wavelength band, in particular, light in a blue band or a violet band of the visible range can be emitted.

The processor device 33 acquires an endoscopic image from the image sensor 41 or comprises an endoscopic image generation unit 48 that generates an endoscopic image obtained by performing image processing on the endoscopic image acquired from the image sensor 41. The image sensor 41 and the endoscopic image generation unit 48 form an "endoscopic image acquisition unit" in the endoscope apparatus 21. The endoscopic image acquisition unit acquires an endoscopic image including a subject image by imaging the subject using illumination light. The medical image processing apparatus 10 is connected to the processor device 33. The medical image acquisition unit 11 acquires the endoscopic image directly from the endoscopic image generation unit 48 of the endoscope apparatus 21.

Figure 3:
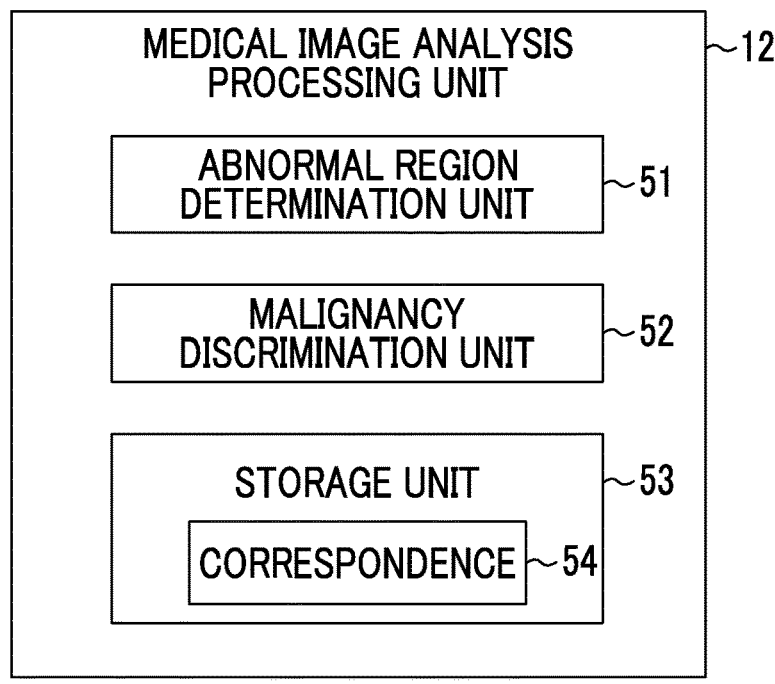
FIG. 3 is a block diagram of a medical image analysis processing unit.

The medical image analysis processing unit 12 performs an analysis process using an endoscopic image that is a medical image acquired by the medical image acquisition unit 11 (hereinafter, simply referred to as an endoscopic image). Specifically, as shown in FIG. 3, the medical image analysis processing unit includes an abnormal region determination unit 51, a malignancy discrimination unit 52, and a storage unit 53.

The abnormal region determination unit 51 determines an abnormal region by using a medical image acquired by the medical image acquisition unit 11 (hereinafter, referred to as an abnormal region determination process). The abnormal region is a region to be noted (a region referred to as a so-called region of interest, attention region, or abnormal region, hereinafter referred to as an abnormal region) including one or a plurality of portions in which an abnormality such as a lesion is recognized (a lesion portion or a portion possibly having a lesion). The abnormal region determination unit 51 calculates one or a plurality of predetermined feature amounts, and determines an abnormal region by using the calculated feature amounts. In addition, the abnormal region determination unit 51 can determine an abnormal region by texture analysis or pattern matching using a regular shape instead of using the feature amount.

In a case where the medical image acquisition unit 11 acquires an endoscopic image, the abnormal region is a region including a target such as one or a plurality of lesions, a region having a feature of a color or shape different from that of a surrounding tissue, a region in which a medicine is dispersed, or a region in which a treatment (a biopsy, an endoscopic mucosal resection (EMR), an endoscopic submucosal dissection (ESD), or the like) is performed. In a case where the medical image is an endoscopic image, the lesion or the like is, for example, a polyp (a raised lesion), and more specifically, a hyperplastic polyp (HP), a sessile serrated adenoma/polyp (SSA/P), an adenoma, a cancer, or the like. In addition, the region having a feature of a color or shape different from that of the surrounding tissue or the like is a redness, an atrophy, a diverticulum, a treatment mark, or the like of the subject.

In the abnormal region determination process, at least the presence or absence of an abnormal region is determined. In the abnormal region determination process, in addition to the above description, the position, size, area, color, and the like of the abnormal region can be determined. In addition, the abnormal region determination unit 51 can include a "probability" indicating a likelihood of each determination in the result of the abnormal region determination process.

In the abnormal region determination process, it is determined whether or not there is an abnormal region for some or all of the medical images. That is, the abnormal region determination unit 51 can perform an abnormal region determination process for each pixel, for each small region in a case of dividing an endoscopic image into small regions, or for the entire endoscopic image.

In the abnormal region determination process, one or a plurality of locations of each medical image may be determined as an abnormal region. The abnormal region determination unit 51 can use one or a plurality of medical images in the abnormal region determination process. The abnormal region determination unit 51 may use a medical image not used for display in the abnormal region determination process. In the abnormal region determination process, a medical image captured using special light having a spectrum different from that of white light may be used.

The malignancy discrimination unit 52 discriminates the degree of malignancy of an abnormality included in the abnormal region (hereinafter, referred to as a lesion or the like). More specifically, the malignancy discrimination unit 52 discriminates the type of a lesion or the like or the degree of progress of the lesion or the like, and determines the degree of malignancy by using the discriminated type or degree of progress of the lesion or the like. The degree of malignancy is an evaluation indicating an importance in diagnosis of a lesion or the like, which reflects at least the type of the lesion or the like or the degree of progress of the lesion or the like (the progress status in a case where the "lesion or the like" is a treatment scar or the like).

For example, in a case where the lesion or the like is a polyp, the malignancy discrimination unit 52 discriminates any of a hyperplastic polyp, SSA/P, an adenoma, or a cancer, as the type of the lesion or the like. In addition, in a case where the lesion or the like is a cancer, the degree of progress of the lesion or the like is discriminated by an endoscopic finding classification. For example, in the case of colorectal tumor, the endoscopic finding classification includes the narrow-band imaging international colorectal endoscopic (NICE) classification, the Japan narrow band imaging (NBI) expert team (JNET) classification, or the like. In addition, even in a case where the lesion or the like is an inflammatory bowel disease, the degree of progress of the lesion or the like is discriminated by the endoscopic finding classification. For example, in ulcerative colitis, which is one of the inflammatory bowel diseases, the endoscopic finding classification includes, for example, Mayo classification or Matts classification.

The malignancy discrimination unit 52 calculates one or a plurality of predetermined feature amounts, and discriminates the type or the degree of progress of a lesion or the like by using the calculated feature amounts. In addition, the malignancy discrimination unit 52 can discriminate the type or the degree of progress of the lesion or the like by texture analysis or pattern matching using a regular shape instead of using the feature amount.

The malignancy discrimination unit 52 obtains the degree of malignancy from the discriminated type of the lesion or the like or the discriminated degree of progress of the lesion or the like by using a correspondence 54 stored in the storage unit 53. The storage unit 53 stores the correspondence 54 that associates the type of the lesion or the like or the degree of progress of the lesion or the like with the degree of malignancy. The correspondence 54 is, for example, a conversion table for converting the type of the lesion or the like or the degree of progress of the lesion or the like into the degree of malignancy, or a parameter of a function for calculating the degree of malignancy from the type of the lesion or the like or the degree of progress of the lesion or the like. The degree of malignancy is, for example, a numerical value, and for example, in a case where a polyp is a determination target, the degree of malignancy of normal (a case where there is no polyp) can be obtained as "0", and the degree of malignancy of a cancer can be obtained as "100 to 200" depending on the stage. The degree of malignancy is determined in a relative and stepwise manner according to the type or the degree of progress of the lesion or the like. For this reason, in a case where the type or the degree of progress of the lesion or the like is different, the degree of malignancy is different.

The display unit 13 is a display for displaying a medical image acquired by the medical image acquisition unit 11, a determination result of an abnormal region, and the like. In addition, in a case where the medical image acquisition unit 11 acquires a plurality of medical images, the display unit 13 can present a display list of the plurality of medical images. A monitor or a display included in a device or the like to which the medical image processing apparatus 10 is connected can be shared and used as the display unit 13 of the medical image processing apparatus 10.

The display control unit 15 controls a display form of the medical image and the analysis result on the display unit 13. Specifically, the display control unit 15 emphasizes or suppresses display of at least some medical images among the plurality of medical images by using the degree of malignancy, in displaying the plurality of medical images on the display unit 13. As a result, the display control unit 15 emphasizes display of a medical image to be preferentially diagnosed, such as a medical image having a high necessity for diagnosis or the like or a medical image having a high importance in diagnosis or the like. For example, in a case of presenting a display list of a plurality of medical images, by arranging the plurality of medical images in order of the degree of malignancy, a medical image having a faster display order is relatively emphasized as compared with other medical images, or a medical image having a slower display order is relatively suppressed as compared with other medical images. Although depending on the specific form or setting of the display unit 13, the "faster display order" refers to, for example, on the display unit 13, displaying above the other medical images or displaying on the left side of the other medical images. The "slower display order" refers to, for example, on the display unit 13, displaying below the other medical images or displaying on the right side of the other medical images.

In addition, the display control unit 15 can emphasize or suppress display of at least some medical images among the plurality of medical images by adding an emphasis flag to the medical image, adding a character to the medical image, adjusting a display color of the medical image, or adjusting a display size of the medical image. The emphasis flag includes a mark (sign), symbol, emblem, and the like having distinguishability from other medical images, and is, for example, an emphasis frame 57 (see FIG. 8) or an emphasis mark 58 (see FIG. 9).

By adding the emphasis flag, the medical image with the emphasis flag can be relatively emphasized with respect to other medical images. In addition, the medical image without the emphasis flag is relatively inconspicuous with respect to the medical image with the emphasis flag, and as a result, the display of the medical image without the emphasis flag is suppressed. The "character" added to the medical image is, for example, a message that directly prompts a diagnosis or the like, or a character string that indirectly prompts a diagnosis or the like by indicating the type or the degree of progress of an abnormality included in the medical image. In addition, the "character" added to the medical image includes, for example, a negative message indicating that the necessity of a diagnosis or the like is low. The messages and the like consequently emphasize or suppress the display of some medical images. The adjustment of the display color refers to changing a color of some or all of the medical images from the original color of the medical images, and includes temporarily or continuously changing the brightness (brightness, luminance, or the like) of some or all of the medical images. The conspicuous display color emphasizes the display of the medical image, and the Inconspicuous display color suppresses the display of the medical image. The adjustment of the display size refers to relatively enlarging or reducing with respect to other medical images. The enlargement of the display size emphasizes the display of the medical image, and the reduction of the display size suppresses the display of the medical image.

The input receiving unit 16 receives inputs from a mouse, a keyboard, and other operation devices connected to the medical image processing apparatus 10. An operation of each unit of the medical image processing apparatus 10 can be controlled using the operation devices.

The overall control unit 17 controls the overall operation of each unit of the medical image processing apparatus 10. In a case where the input receiving unit 16 receives an operation input using an operation device, the overall control unit 17 controls each unit of the medical image processing apparatus 10 according to the operation input.

The storage unit 18 stores the determination result of the abnormal region, the discrimination result of the type or the degree of progress of the abnormality included in the abnormal region, the degree of malignancy, and the like, as necessary, in a storage device (not shown) such as a memory included in the medical image processing apparatus 10 or a storage device (not shown) included in a medical apparatus such as the endoscope apparatus 21 or the PACS 22.

Figure 4:
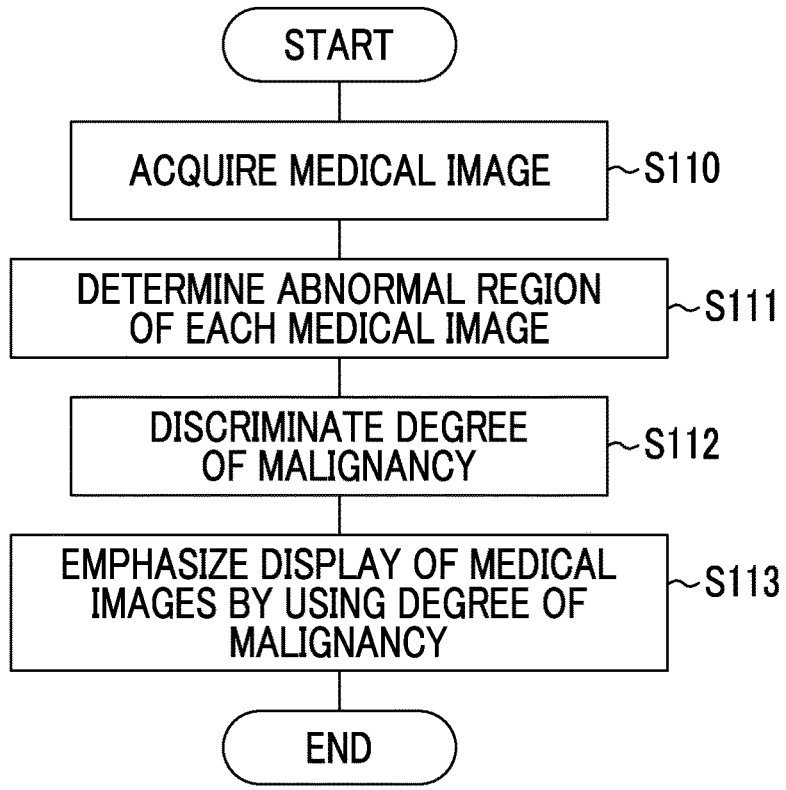
FIG. 4 is a flowchart showing an operation of the medical image processing apparatus.

Hereinafter, a flow of the operation of the medical image processing apparatus 10 will be described. As shown in FIG. 4, the medical image acquisition unit 11 acquires a plurality of endoscopic images automatically or by manual selection (step S110). In the present embodiment, endoscopic images 61, 62, 63, 64, 65, 66, 67, 68, and 69 shown in FIG. 5, the endoscopic images 74, 81, 88, and 91 shown in FIG. 6, and the like are acquired.

In a case where the medical image acquisition unit 11 acquires a medical image, the abnormal region determination unit 51 determines an abnormal region of each medical image (step S111). In the present embodiment, the endoscopic image 91 has an abnormal region X1 (see FIG. 6), the endoscopic image 74 has an abnormal region X2 (see FIG. 6), the endoscopic image 88 has an abnormal region X3 (see FIG. 6), the endoscopic image 66 has an abnormal region X4 (see FIG. 5), and the endoscopic image 81 has an abnormal region X5 (see FIG. 6). The other medical images such as the endoscopic image 61 have no abnormal region.

In a case where the abnormal region determination unit 51 determines an abnormal region, the malignancy discrimination unit 52 discriminates at least an abnormality included in each of the abnormal regions X1 to X5, that is, the degree of malignancy of each lesion or the like (step S112). In the present embodiment, the degree of malignancy of the abnormal region X1 is highest, then the degree of malignancy of each of the abnormal region X2, the abnormal region X3, and the abnormal region X4 is high in this order, and the degree of malignancy of the abnormal region X5 is lowest among the abnormal regions X1 to X5.

In a case where the malignancy discrimination unit 52 discriminates the degree of malignancy, the display control unit 15 presents a display list of some or all of the medical images acquired by the medical image acquisition unit 11 on a display screen of the display unit 13, and emphasizes display of the medical images by using the degree of malignancy, in presenting the display list (step S113).

Figure 5:
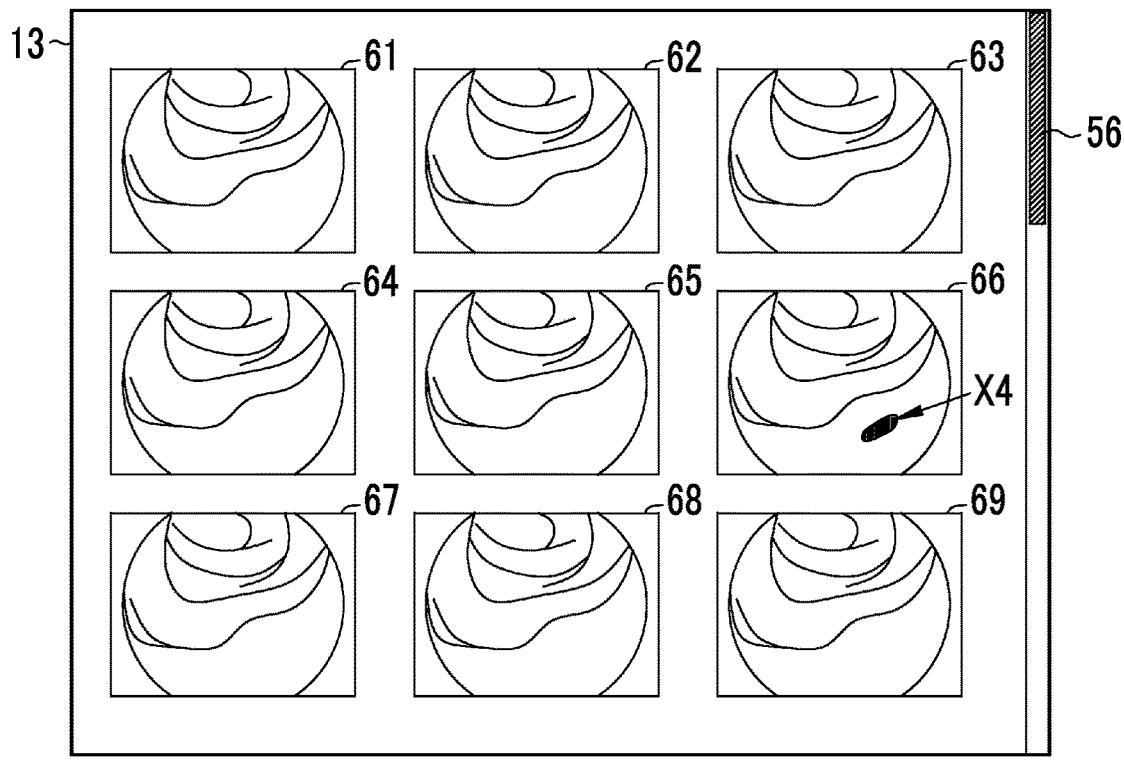
FIG. 5 is an example of a display list of medical images arranged in a time-series order of imaging.

For example, as shown in FIG. 5, in a case where the endoscopic image 61 and the like are presented as a display list in order of the imaging time, the display order of the endoscopic image 61 and the like having the earlier imaging time is earlier. Therefore, among the endoscopic image 61 and the like acquired by the medical image acquisition unit 11, some or all of the endoscopic images having an abnormal region, such as the endoscopic image 66 (in FIG. 6, the endoscopic image 91 having an abnormal region other than the endoscopic image 66, and the like) cannot be found unless the display screen is shifted using a scroll bar 56, for example. In addition, even in a case where the display screen is shifted using the scroll bar 56 and the endoscopic image 91 and the like having an abnormal region are searched for, since it is necessary to check the presence or absence of an abnormal region including the endoscopic image 61 and the like having no abnormal region, it becomes a burden on a doctor or the like.

Figure 6:
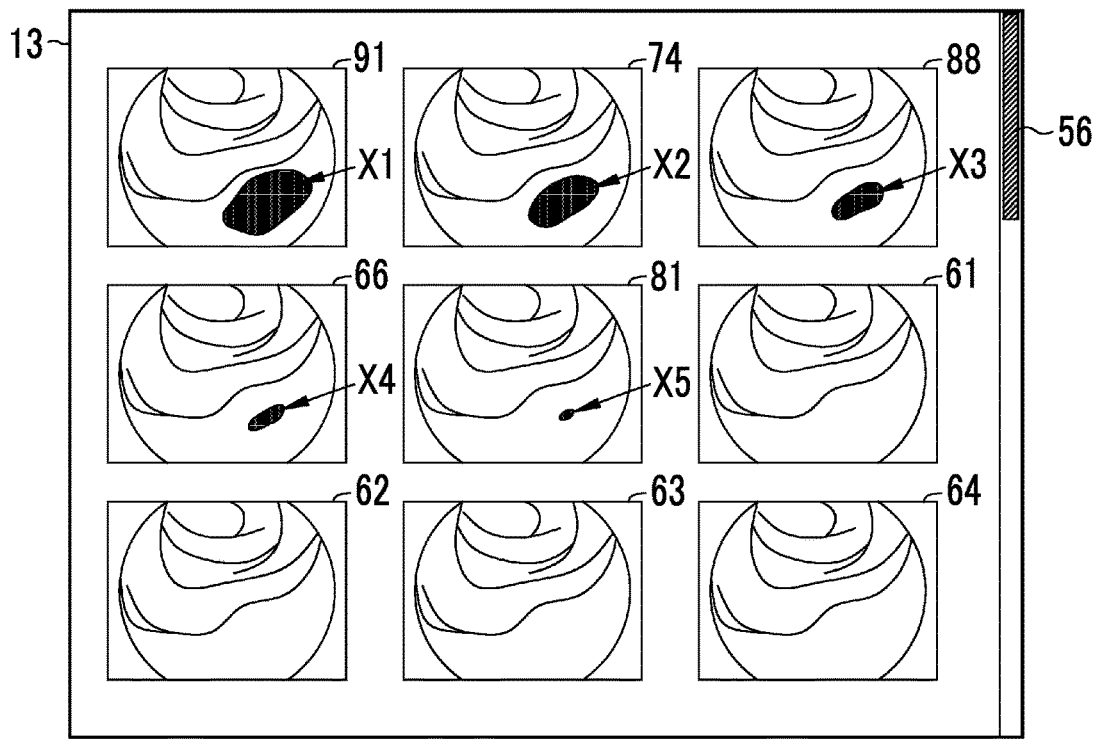
FIG. 6 is an example of a display list of the medical images arranged in order of the degree of malignancy.

Meanwhile, in the medical image processing apparatus 10, for example, as shown in FIG. 6, the display control unit 15 arranges the endoscopic image 91 and the like and presents a display list of the endoscopic images in descending order of the degree of malignancy. That is, the display control unit 15 emphasizes the endoscopic image 91 and the like having an abnormal region by preferentially displaying them more than the endoscopic image 61 and the like having no abnormal region, regardless of the imaging time. Thereby, a doctor or the like can more easily find the endoscopic image 91 and the like having an abnormal region than the endoscopic image 61 having no abnormal region. In addition, even in a case where the endoscopic image 91 and the like having an abnormal region are examined, since the display control unit 15 preferentially displays the endoscopic image having a higher degree of malignancy, a doctor or the like can easily perform a diagnosis or the like by observing the endoscopic image 91 and the like in order in which the display control unit 15 presents a display list of the endoscopic images.

As described above, since the medical image processing apparatus 10 presents a display list of a plurality of medical images by using the degree of malignancy of a lesion or the like, compared with a medical image processing apparatus or the like in the related art, medical images necessary for diagnosis or the like can be selected more quickly and accurately than before. Instead of sorting the display order of the medical images according to one determination material in the diagnosis of redness of a subject or the like, by making it easier to found a medical image with a high degree of malignancy according to the "the degree of malignancy" which is a comprehensive determination criterion more suited to the actual situation of the diagnosis, oversight of the degree of malignancy can be more reliably prevented.

Figure 7:
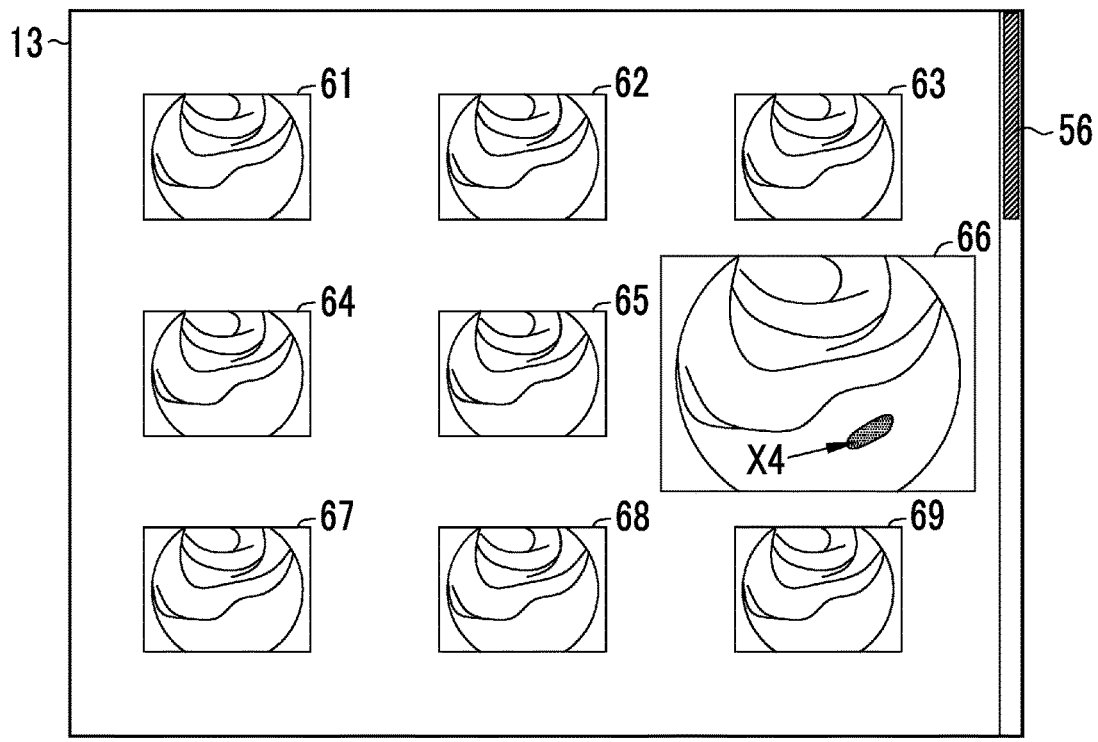
FIG. 7 is an example of a display list in which some endoscopic images are enlarged or reduced.

In the first embodiment described above, the display control unit 15 sorts the medical images to be displayed on the display unit 13 in order of the degree of malignancy and presents a display list of the medical images. However, instead of sorting the medical images to be displayed on the display unit 13 in order of the degree of malignancy, or by sorting the medical images in order of the degree of malignancy and furthermore, relatively enlarging or reducing the medical images, the display control unit 15 can emphasize display of a medical image with a high degree of malignancy. For example, as shown in FIG. 7, in a case of displaying the endoscopic image 61 in order of the imaging time, the display control unit 15 can emphasize display of the endoscopic image 66 by relatively enlarging the endoscopic image 66 including a lesion or the like with a higher degree of malignancy as compared with the endoscopic image 61 having no abnormal region. This makes it possible to easily find the endoscopic image 66 to be noticed in diagnosis or the like, among the endoscopic image 61 and the like presented as a display list on the display screen. In FIG. 7, as compared with the display form of FIG. 5, the endoscopic image 66 having the abnormal region X4 is enlarged, and the endoscopic image 61 having no abnormal region is reduced. However, in a case where at least one of the enlargement of the endoscopic image 66 having the abnormal region X4 or the reduction of the endoscopic image 61 and the like having no abnormal region is performed, the display of the endoscopic image 66 can be relatively emphasized. Here, the medical image having an abnormal region is displayed larger at least than the medical image having no abnormal region.

Note that the display control unit 15 can set an enlargement ratio or a reduction ratio of the medical image by using the degree of malignancy. For example, in a case where the enlargement ratio increases as the degree of malignancy increases, and the reduction ratio increases as the degree of malignancy decreases, since a medical image including a lesion or the like with a higher degree of malignancy becomes relatively conspicuous, a doctor or the like can more quickly and accurately select medical images necessary for diagnosis or the like.

Figure 8:
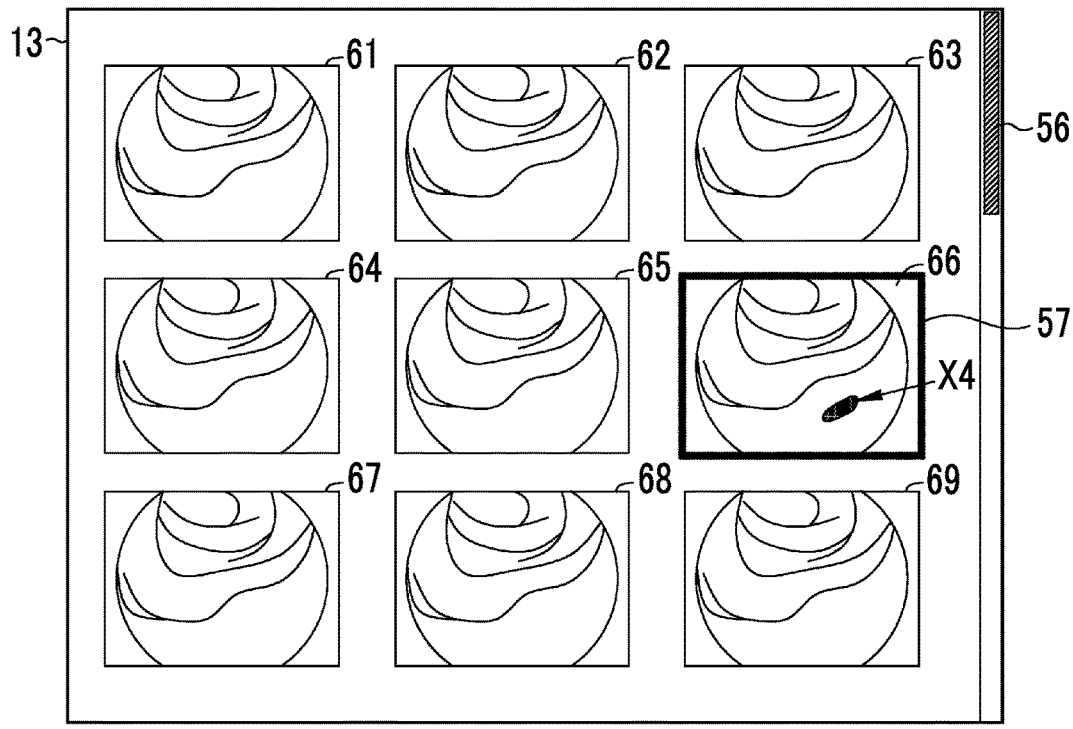
FIG. 8 is an example of a display list in which an emphasis frame is added to some endoscopic images.
Figure 9:
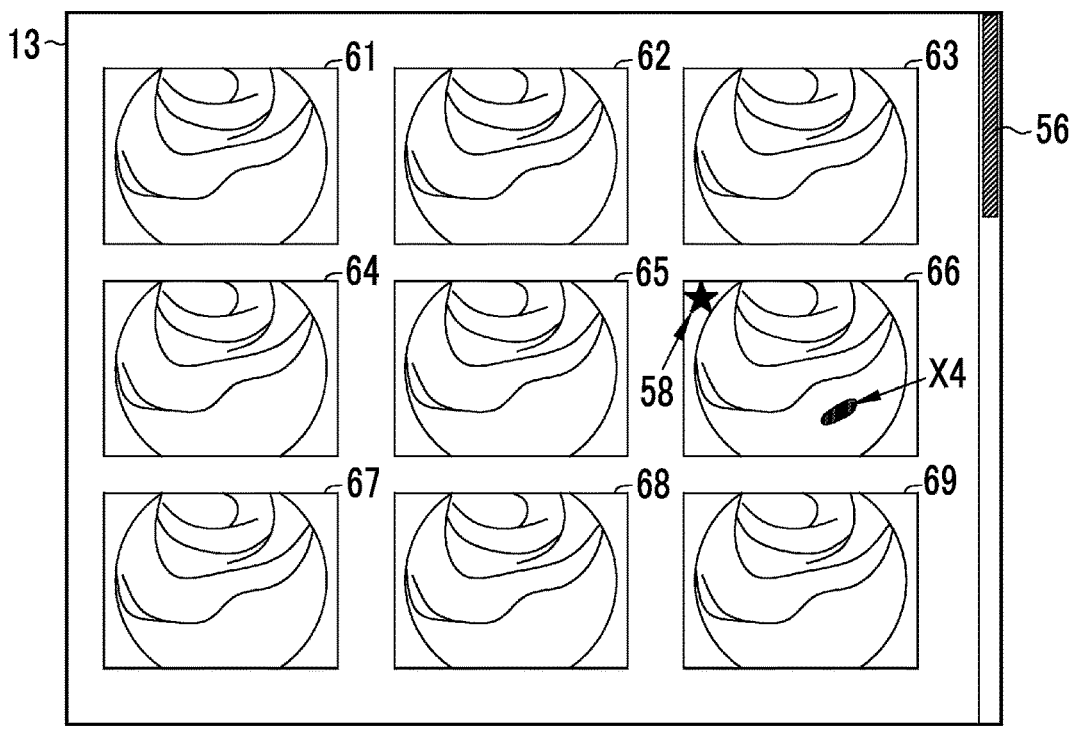
FIG. 9 is an example of a display list in which an emphasis mark is added to some endoscopic images.

In the first embodiment described above, the display control unit 15 sorts of the medical images to be displayed on the display unit 13 in order of the degree of malignancy and presents a display list of the medical images. However, the display control unit 15 can emphasize the display of the endoscopic image 66 and the like having an abnormal region by adding an emphasis flag. For example, as shown in FIG. 8, by adding the emphasis frame 57 to the endoscopic image 66 including a lesion or the like with a high degree of malignancy, the endoscopic image 66 can be relatively emphasized compared with the endoscopic image 61 and the like having no abnormal region. In addition, as shown in FIG. 9, by adding the emphasis mark 58 to the endoscopic image 66 including a lesion or the like with a high degree of malignancy, the endoscopic image 66 can be relatively emphasized compared with the endoscopic image 61 and the like having no abnormal region. As described above, the addition of the emphasis flag makes it possible to easily find the endoscopic image 66 to be noticed in diagnosis or the like, among the endoscopic image 61 and the like presented as a display list on the display screen.

The emphasis display adding the emphasis flag can be performed instead of sorting using the degree of malignancy or relative enlargement using the degree of malignancy, or in combination therewith. The shape, color, thickness, size, or the like of the emphasis frame 57 or the emphasis mark 58 can be set using the degree of malignancy. For example, in a case where the emphasis frame 57 or the emphasis mark 58 is changed according to the degree of malignancy, since the degree of malignancy can be easily determined based on the color of the emphasis frame 57 or the emphasis mark 58, a doctor or the like can more quickly and accurately select medical images necessary for diagnosis or the like.

Figure 10:
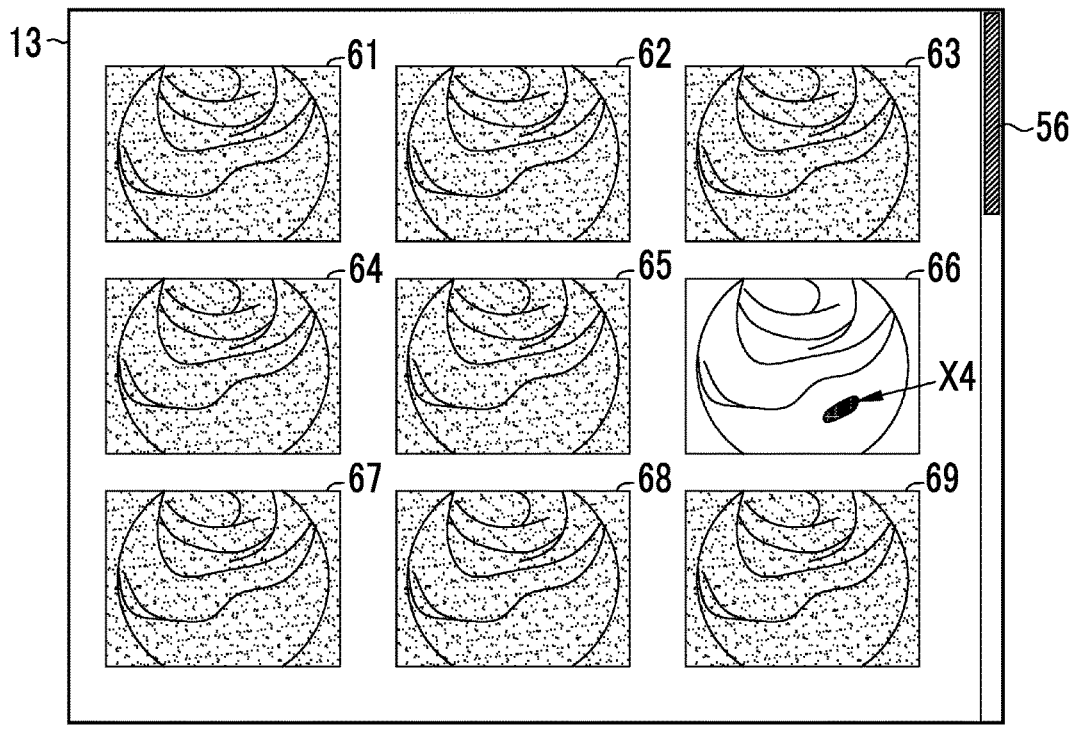
FIG. 10 is an example of a display list in which a display color of some endoscopic images is adjusted.

In the first embodiment described above, the display control unit 15 sorts the medical images to be displayed on the display unit 13 in order of the degree of malignancy and presents a display list of the medical images. However, the display control unit 15 can emphasize the display of the endoscopic image 66 and the like having an abnormal region by adjusting a display color. For example, as shown in FIG. 10, by graying out the endoscopic image 61 having no abnormal region, the endoscopic image 66 including a lesion or the like with a high degree of malignancy can be relatively emphasized.

The emphasis display with the adjustment of the display color can be performed instead of sorting using the degree of malignancy, relative enlargement using the degree of malignancy, or the emphasis display adding the emphasis flag, or in combination therewith. In addition, in the modification example described above, although the endoscopic image 61 and the like having no the abnormal region are colored, the endoscopic image 66 and the like including a lesion or the like with a high degree of malignancy can be emphasized by coloring them and making them conspicuous. Of course, by coloring the endoscopic image 61 and the like having no abnormal region and the endoscopic image 66 and the like having an abnormal region with different colors, the endoscopic image 66 and the like including a lesion or the like with a high degree of malignancy can be emphasized. In a case where the emphasis display with the adjustment of the display color is performed, the display color of the medical image can be set using the degree of malignancy. In a case where the display color of the medical image is set using the degree of malignancy, since the degree of malignancy can be easily determined based on the display color of the medical image, a doctor or the like can more quickly and accurately select medical images necessary for diagnosis or the like.

Second Embodiment

In a case where an examination is performed using a medical apparatus such as the endoscope apparatus 21, an abnormality such as a lesion or the like may be imaged multiple times under different imaging conditions, for example, and a plurality of medical images each including the same abnormality may be acquired. Since the images capture the same abnormality, basically, the degrees of malignancy discriminated by the malignancy discrimination unit 52 are almost the same (different but close values). However, the ease of use in diagnosis (such as the ease of observing a lesion or the like) differs depending on the imaging conditions. Therefore, it is desirable to preferentially emphasize the display of the medical image easier to use in diagnosis, rather than equally emphasize the display of the medical images.

Figure 11:
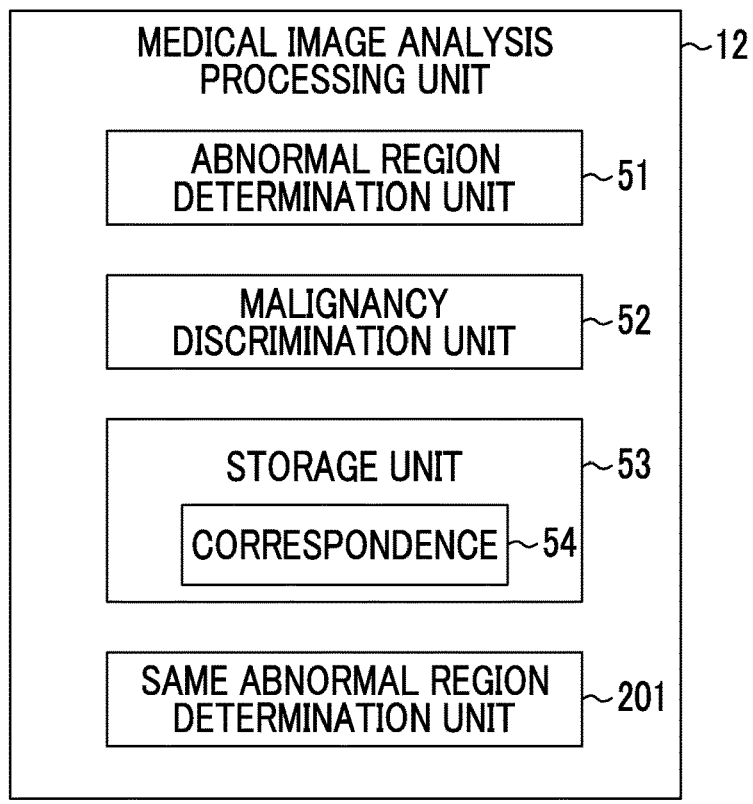
FIG. 11 is a block diagram of a medical image analysis processing unit in a second embodiment.

For this reason, in the present second embodiment, as shown in FIG. 11, the medical image analysis processing unit 12 includes a same abnormal region determination unit 201 in addition to the abnormal region determination unit 51, the malignancy discrimination unit 52, and the storage unit 53. Other configurations are the same as those of the first embodiment.

The same abnormal region determination unit 201 determines whether or not the plurality of medical images acquired by the medical image acquisition unit 11 each have the abnormal region including the same abnormality. The "same abnormality" means that the targets to be determined as abnormal are the same target. For example, although the endoscopic image 66 has the abnormal region X4, an endoscopic image obtained by capturing a lesion or the like included in the abnormal region X4 at a distance, angle, brightness, or the like which is different from the endoscopic image 66 includes the same abnormality as the endoscopic image 66. Meanwhile, even in a case where a lesion or the like included in the abnormal region X4 of the endoscopic image 66 is a cancer, and a lesion or the like included in the abnormal region X1 of the endoscopic image 91 is a cancer, in a case where the cancer in the abnormal region X4 and the cancer in the abnormal region X1 are different cancers located at different positions in the intestinal tract, the endoscopic image 66 and the endoscopic image 91 do not include the same abnormality because the same target is not imaged. In addition, the same abnormal region determination unit 201 performs the same abnormal region determination process by combining one or more of a feature amount (color information, brightness values, and the like) calculated using a medical image, a similarity, a movement vector indicating a direction and a magnitude of a movement, a closeness of an imaging time of medical images to be compared, and the like.

In a case where there are two or more medical images each having the abnormal region including the same abnormality, the display control unit 15 emphasizes or suppresses display of at least some medical images among the two or more medical images each having the abnormal region including the same abnormality by using the degree of malignancy and an imaging distance of the medical image. For example, the display control unit 15 emphasizes or suppresses display of the medical image having a relatively short imaging distance, among the two or more medical images each having the abnormal region including the same abnormality, or emphasizes or suppresses display of the medical image having a relatively long imaging distance, among the two or more medical images each having the abnormal region including the same abnormality. More specifically, for example, depending on the type or the degree of progress of the lesion or the like, the display control unit 15 emphasizes display of the medical image having a relatively short imaging distance, or suppresses display of the medical image having a relatively long imaging distance, among the two or more medical images each having the abnormal region including the same abnormality. In addition, depending on the type or the degree of progress of the lesion or the like, the display control unit 15 emphasizes the display of a medical image of which imaging distance is close to a predetermined imaging distance (appropriate imaging distance) determined for each imaging region (such as esophagus, stomach, or large intestine) in comparison with the display of other medical images, or suppresses the display of a medical image of which imaging distance is far to a predetermined imaging distance determined for each imaging region in comparison with the display of other medical images, among the two or more medical images each having the abnormal region including the same abnormality.

Note that the imaging distance is the distance between the endoscope 31 and the subject in the case of the endoscope apparatus 21, and is the substantial distance, which includes an imaging magnification, between the endoscope 31 and the subject in a case where the endoscope 31 has a zoom function. The display control unit 15 acquires the imaging distance of the medical image from a header or the like of the medical image, the PACS 22, or the medical apparatus that has captured the medical image, such as the endoscope apparatus 21.

Figure 12:
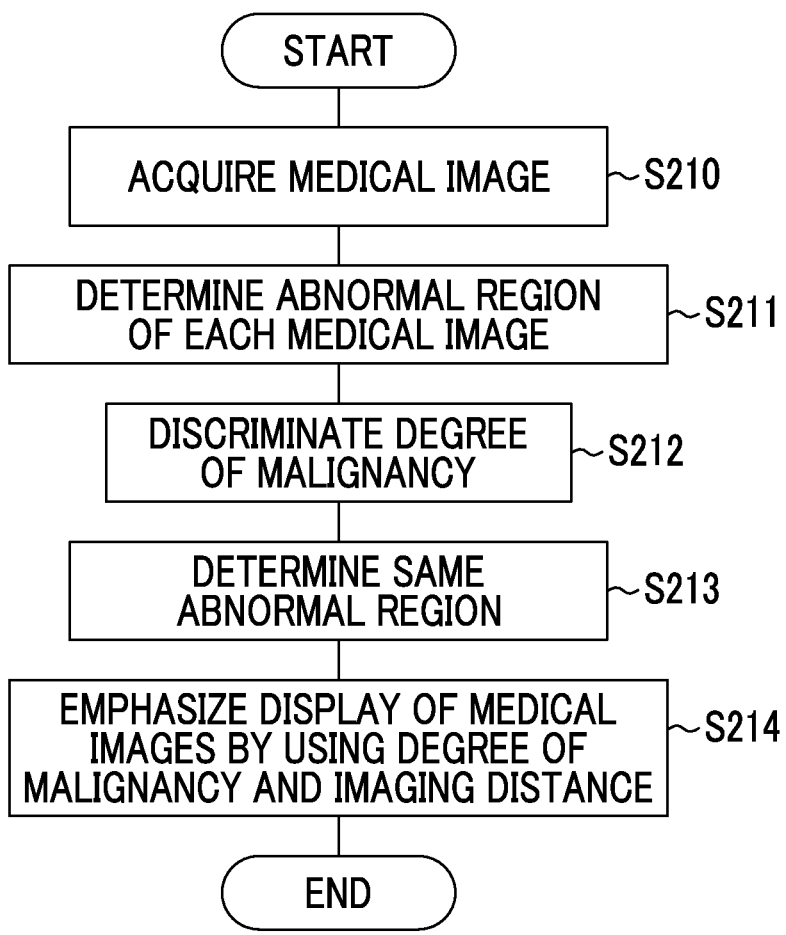
FIG. 12 is a flowchart showing an operation of a medical image processing apparatus according to the second embodiment.

Hereinafter, a flow of the operation of the medical image processing apparatus 10 including the same abnormal region determination unit 201 will be described. As shown in FIG. 12, the medical image acquisition unit 11 acquires a plurality of endoscopic images automatically or by manual selection (step S210). In the present embodiment, the medical image acquisition unit 11 acquires a plurality of endoscopic images including at least an endoscopic image 211, an endoscopic image 212, and an endoscopic image 213 shown in FIG. 13.

The endoscopic image 211, the endoscopic image 212, and the endoscopic image 213 are all endoscopic images obtained by capturing an abnormal region X20. Here, the imaging distances of the endoscopic image 211, the endoscopic image 212, and the endoscopic image 213 are different from each other. The endoscopic image 211 is an endoscopic image having the shortest imaging distance among the endoscopic image 211, the endoscopic image 212, and the endoscopic image 213. The endoscopic image 212 is an endoscopic image having the second shortest imaging distance, and the endoscopic image 213 is an endoscopic image having the longest imaging distance among the endoscopic image 211, the endoscopic image 212, and the endoscopic image 213.

In a case where the medical image acquisition unit 11 acquires a medical image, the abnormal region determination unit 51 determines an abnormal region of each medical image (step S211) and the malignancy discrimination unit 52 discriminates the degree of malignancy (step S212). Thereafter, the same abnormal region determination unit 201 determines whether or not each medical image has the abnormal region including the same abnormality (step S213). In the present embodiment, the endoscopic image 211, the endoscopic image 212, and the endoscopic image 213 each have the same abnormal region X20.

Figure 13:
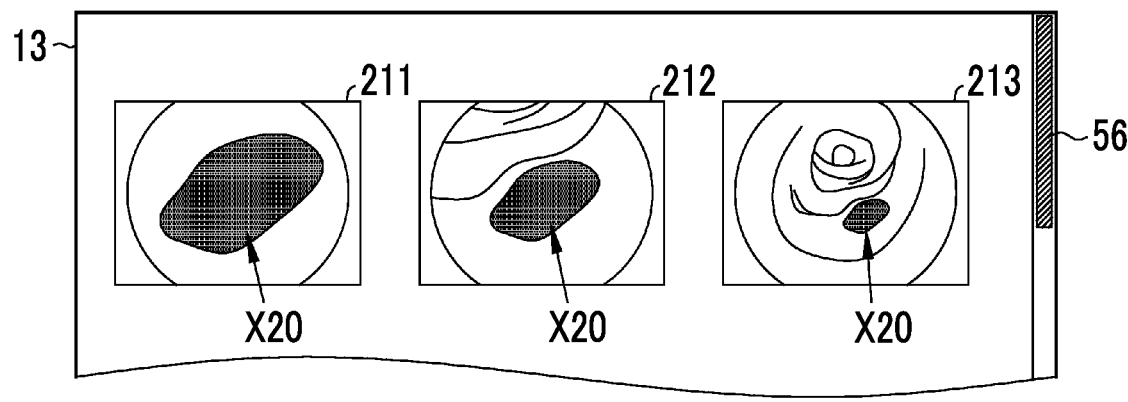
FIG. 13 is an example of a display list of endoscopic images arranged in order of an imaging distance.

The display control unit 15 presents a display list of a plurality of endoscopic images on the display unit 13 by using the degree of malignancy and the imaging distance (step S214). For example, as shown in FIG. 13, the display control unit 15 sorts and displays a plurality of endoscopic images in order of the degree of malignancy, for example, as in the first embodiment. Regarding the arrangement order of the endoscopic image 211, the endoscopic image 212, and the endoscopic image 213 each having the same abnormal region X20, the degree of malignancy is almost the same because the same abnormal region X20 is included. Accordingly, the endoscopic images are arranged in order of the closest imaging distance.

As described above, in a case where the same abnormal region X20 is determined, and the endoscopic image 211, the endoscopic image 212, the endoscopic image 213 each having the same abnormal region X20 are arranged in order of the imaging distance, the endoscopic image 211 easier to use in diagnosis can be relatively emphasized even in a case where a lesion or the like has almost the same degree of malignancy. As a result, an endoscopic image necessary for diagnosis or the like can be particularly quickly and accurately selected.

Figure 14:
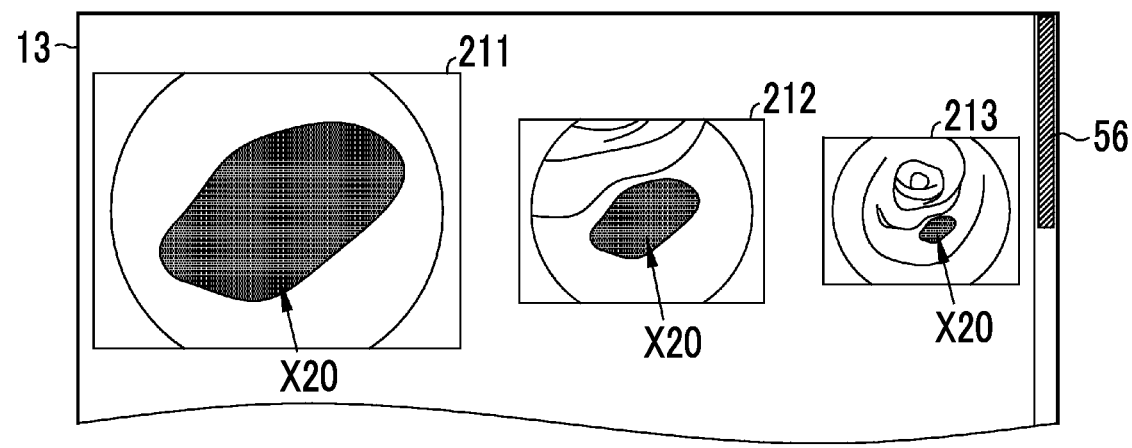
FIG. 14 is an example of a display list in which some endoscopic images are enlarged or reduced in order of the imaging distance.

In the second embodiment described above, the display control unit 15 sorts the plurality of endoscopic images to be displayed on the display unit 13 in order of the degree of malignancy and the imaging distance and presents a display list of the endoscopic images. However, as shown in FIG. 14, the display control unit 15 can relatively enlarge and emphasize the endoscopic image 211 in order of the degree of malignancy and the imaging distance. In the case of adding the emphasis flag for emphasis, the degree of malignancy and the imaging distance can be used in the same manner in the case of adjusting the display color for emphasis.

In the second embodiment, the display control unit 15 can preferentially emphasize display of one or the plurality of medical images of which the imaging distance is relatively close to a reference imaging distance that differs depending on a procedure or suppress display of one or the plurality of medical images of which the imaging distance is relatively far from the reference imaging distance, among the plurality of medical images. The procedure includes screening, diagnosis, treatment, or the like. The reference imaging distance is an imaging distance used as a reference for emphasizing or suppressing display. The reason why the reference imaging distance is set depending on the procedure as described above is that, for example, the purpose of imaging differs between screening, diagnosis, and treatment, so that the appropriate imaging distance differs. In a case where the reference imaging distance is set depending on the procedure as described above, for example, a medical apparatus such as the endoscope apparatus 21 or the PACS 22 records information related to an imaging purpose of each medical image in a header or the like of the medical image, and the display control unit 15 obtains the information related to the imaging purpose of the medical image from the header or the like of the medical image. Then, the display control unit 15 emphasizes the medical image captured at an appropriate imaging distance in comparison with the other medical images. This makes it possible to emphasize the display of an appropriate medical image that matches the purpose of imaging.

In the first embodiment, the second embodiment, and the modification examples described above (hereinafter, referred to as the above-described embodiments and the like), the correspondence 54 is pre-determined, but the correspondence 54 can be set for each patient or for each doctor. This is because a lesion or the like to be diagnosed differs for each patient or for each doctor. In a case where the correspondence 54 is changed, the storage unit 53 stores the changed correspondence 54 automatically or in response to a manual save operation of the setting change using the input receiving unit 16 or the like. For this reason, for example, there is no need to redo the setting of the correspondence 54 for each patient or each doctor for each examination, and the malignancy discrimination unit 52 automatically uses the correspondence 54 after the setting change.

Each unit forming the medical image analysis processing unit 12 in the above-described embodiments and the like can be configured using a so-called artificial intelligence (AI) program learned by machine learning, deep learning, or the like.

Figure 15:
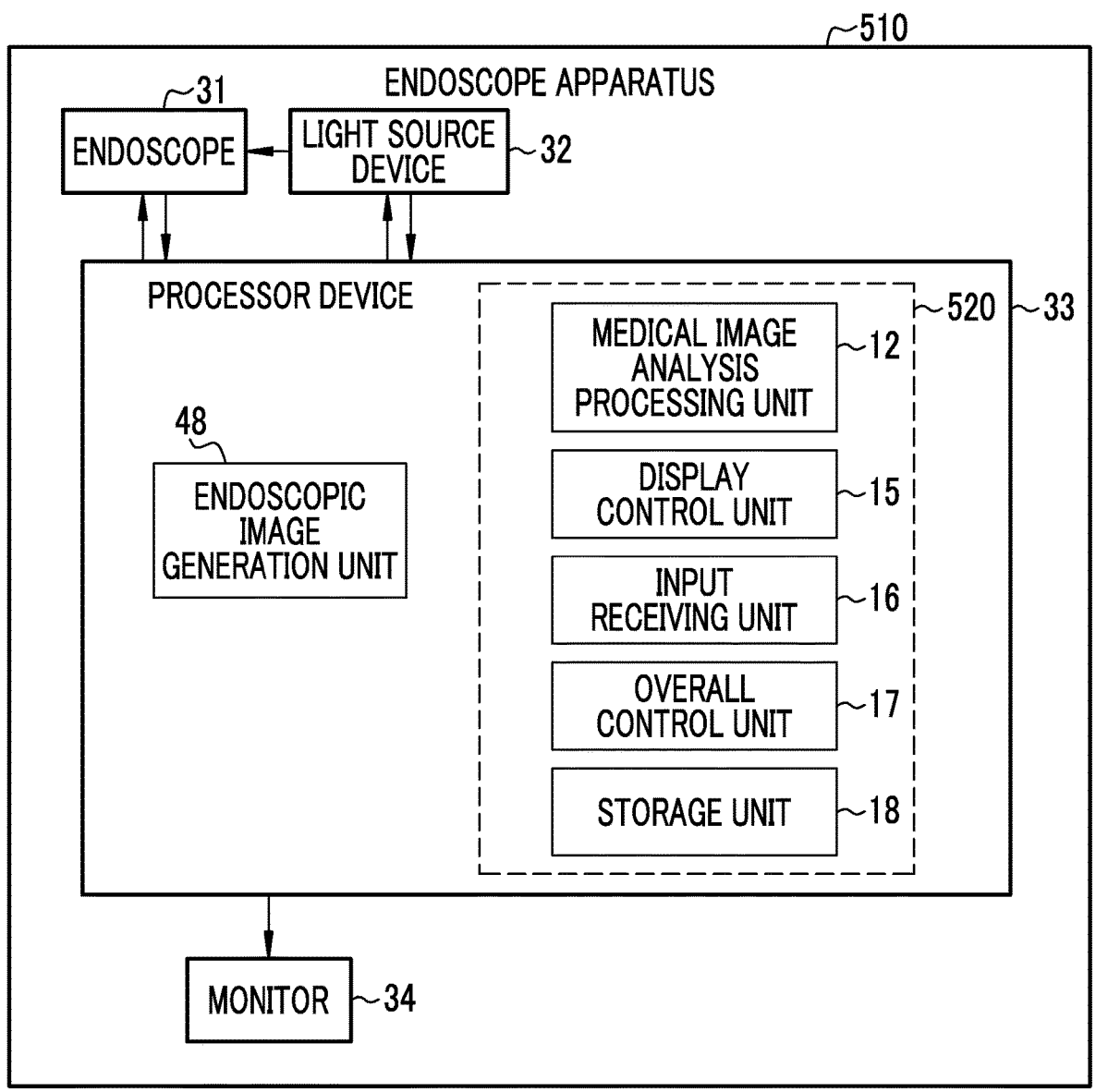
FIG. 15 is a block diagram of an endoscope apparatus including the medical image processing apparatus.

In the above-described embodiments and the like, the medical image processing apparatus 10 and the endoscope apparatus 21 are separate apparatuses. However, the endoscope apparatus 21 can include the medical image processing apparatus 10. In this case, as an endoscope apparatus 510 shown in FIG. 15, each unit 520 forming the medical image processing apparatus 10 is provided in the processor device 33. Here, the display unit 13 can share the monitor 34 of the endoscope apparatus 21. In addition, the medical image acquisition unit 11 corresponds to an "endoscopic image acquisition unit" formed by the image sensor 41 and the endoscopic image generation unit 48. For this reason, it is sufficient to provide the processor device 33 with each unit other than the medical image acquisition unit 11 and the display unit 13. The configuration of each of other units is the same as in the first embodiment. In addition, a new endoscope apparatus can be configured by all of the medical image processing apparatuses 10 of each embodiment described above and other modification examples and the endoscope apparatus 21 shown in FIG. 2.

Figure 16:
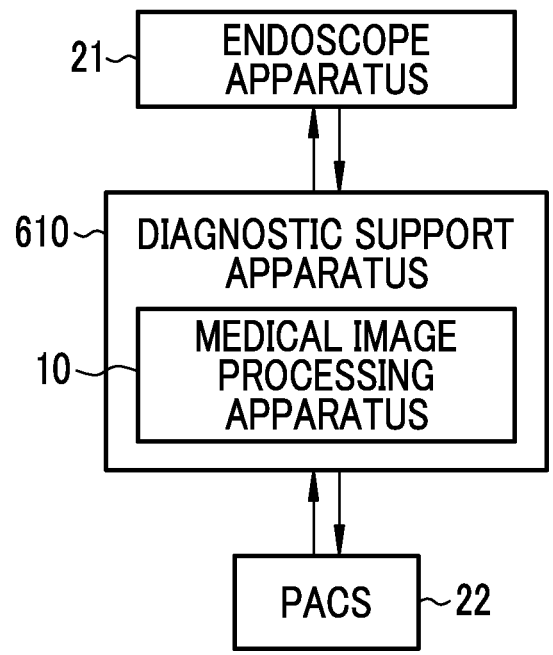
FIG. 16 is an explanatory diagram of a diagnostic support apparatus including the medical image processing apparatus.
Figure 17:
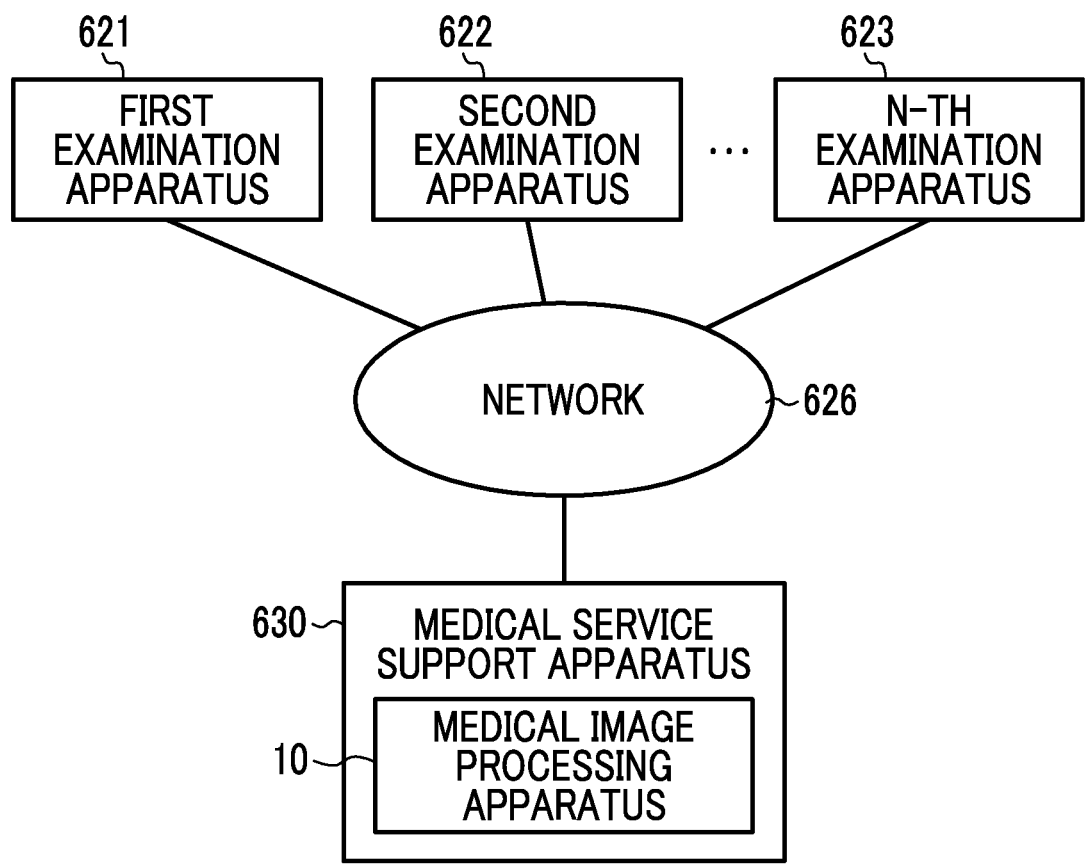
FIG. 17 is an explanatory diagram of a medical service support apparatus including the medical image processing apparatus.

In addition, as shown in FIG. 16, a diagnostic support apparatus 610 used in combination with the endoscope apparatus 21 and other modalities can include the medical image processing apparatuses 10 of the above embodiment and other modification examples. In addition, as shown in FIG. 17, for example, a medical service support apparatus 630 connected to various examination apparatuses including the endoscope apparatus 21, such as a first examination apparatus 621, a second examination apparatus 622, . . . , and an N-th examination apparatus 623, through a certain network 626 can include the medical image processing apparatuses 10 of the above embodiment and other modification examples.

In addition to this, the medical image processing apparatus 10, various apparatuses including the medical image processing apparatus 10, and various apparatuses or systems having a function of the medical image processing apparatus 10 can be used by making the following various changes or the like.

As the medical image, it is possible to use a normal light image obtained by emitting light in a white band or light in a plurality of wavelength bands as light in the white band.

In a case where an image obtained by emitting light in a specific wavelength band is used as the medical image, a band narrower than the white wavelength band can be used as the specific wavelength band.

The specific wavelength band is, for example, a blue band or a green band of a visible range.

In a case where the specific wavelength band is the blue band or the green band of a visible range, it is preferable that the specific wavelength band includes a wavelength band of 390 nm to 450 nm or a wavelength band of 530 nm to 550 nm and that light in the specific wavelength band has a peak wavelength within the wavelength band of 390 nm to 450 nm or the wavelength band of 530 nm to 550 nm.

The specific wavelength band is, for example, a red band of a visible range.

In a case where the specific wavelength band is the red band of a visible range, it is preferable that the specific wavelength band includes a wavelength band of 585 nm to 615 nm or a wavelength band of 610 nm to 730 nm and that light in the specific wavelength band has a peak wavelength within the wavelength band of 585 nm to 615 nm or the wavelength band of 610 nm to 730 nm.

The specific wavelength band can include, for example, a wavelength band in which light absorption coefficients of oxygenated hemoglobin and reduced hemoglobin are different, and light in the specific wavelength band can have a peak wavelength in the wavelength band in which light absorption coefficients of oxygenated hemoglobin and reduced hemoglobin are different.

In a case where the specific wavelength band includes a wavelength band in which the light absorption coefficients of oxygenated hemoglobin and reduced hemoglobin are different and light in the specific wavelength band has a peak wavelength in the wavelength band in which the light absorption coefficients of oxygenated hemoglobin and reduced hemoglobin are different, it is preferable that the specific wavelength band includes a wavelength band of 400±10 nm, 440±10 nm, 470±10 nm, or 600 nm to 750 nm and that light in the specific wavelength band has a peak wavelength within the wavelength band of 400±10 nm, 440±10 nm, 470±10 nm, or 600 nm to 750 nm.

In a case where the medical image is an in-vivo image of the living body, the in-vivo image can have information on fluorescence emitted from the fluorescent material in the living body.

In addition, as the fluorescence, fluorescence obtained by emitting excitation light having a peak wavelength of 390 nm to 470 nm to the inside of the living body can be used.

In a case where the medical image is an in-vivo image of the living body, the wavelength band of infrared light can be used as the specific wavelength band described above.

In a case where the medical image is an in-vivo image of the living body and the wavelength band of infrared light is used as the specific wavelength band described above, it is preferable that the specific wavelength band includes a wavelength band of 790 nm to 820 nm or 905 nm to 970 nm and that light in the specific wavelength band has a peak wavelength within the wavelength band of 790 nm to 820 nm or 905 nm to 970 nm.

The medical image acquisition unit 11 can have a special light image acquisition section that acquires a special light image having a signal in a specific wavelength band on the basis of a normal light image obtained by emitting light in a white band or light in a plurality of wavelength bands as light in the white band. In this case, the special light image can be used as the medical image.

The signal in a specific wavelength band can be obtained by calculation based on the color information of RGB or CMY included in the normal light image.

It is possible to comprise a feature amount image generation unit that generates a feature amount image by calculation based on at least one of the normal light image obtained by emitting light in a white band or light in a plurality of wavelength bands as light in the white band or the special light image obtained by emitting light in a specific wavelength band. In this case, the feature amount image can be used as the medical image.

In the endoscope apparatus 21, a capsule endoscope can be used as the endoscope 31. In this case, the light source device 32 and a part of the processor device 33 can be mounted in the capsule endoscope.

In the above-described embodiments and the like, hardware structures of processing units for executing various kinds of processing, such as the medical image acquisition unit 11, the medical image analysis processing unit 12 (each unit forming the medical image analysis processing unit 12), the display control unit 15, the input receiving unit 16, the overall control unit 17, and the endoscopic image generation unit 48 of the endoscope apparatus 21, are various processors shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a dedicated circuit configuration for executing various types of processing, and the like.

One processing unit may be configured by one of various processors, or may be configured by a combination of two or more processors of the same type or different types (for example, a combination of a plurality of FPGAs or a combination of a CPU and an FPGA). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: medical image processing apparatus
11: medical image acquisition unit
12: medical image analysis processing unit
13: display unit
15: display control unit
16: input receiving unit
17: overall control unit
18: storage unit
21, 510: endoscope apparatus
22: PACS
31: endoscope
32: light source device
33: processor device
34: monitor
41: image sensor
42: light source unit
47: light source control unit
48: endoscopic image generation unit
51: abnormal region determination unit
52: malignancy discrimination unit
53: storage unit
54: correspondence
56: scroll bar
57: emphasis frame
58: emphasis mark
61 to 69, 74, 81, 88, 91, 211 to 213: endoscopic image
201: same abnormal region determination unit
520: each unit forming medical image processing apparatus
610: diagnostic support apparatus
621: first examination apparatus
622: second examination apparatus
623: N-th examination apparatus
626: network
630: medical service support apparatus
X1 to X5, X20: abnormal region
S110 to S113, S210 to S214: steps of operation

What is claimed is:

1. A medical image processing apparatus comprising:
a processor configured to function as:
a medical image acquisition unit that acquires a plurality of medical images, wherein each medical image includes a subject image;
an abnormal region determination unit that determines an abnormal region of each medical image;
a malignancy discrimination unit that discriminates a degree of malignancy of an abnormality included in the abnormal region; and
a display control unit that emphasizes or suppresses display of at least some medical images among the plurality of medical images by using the degree of malignancy, in displaying the plurality of medical images on a display,
wherein the malignancy discrimination unit discriminates a type of the abnormality or a degree of progress of the abnormality included in the abnormal region, and determines the degree of malignancy by using the type of the abnormality or the degree of progress of the abnormality.

2. The medical image processing apparatus according to claim 1, further comprising:
a storage that stores a correspondence that associates the type of the abnormality or the degree of progress of the abnormality with the degree of malignancy,
wherein the malignancy discrimination unit obtains the degree of malignancy from the type of the abnormality or the degree of progress of the abnormality by using the correspondence stored in the storage.

3. The medical image processing apparatus according to claim 2,
wherein the correspondence is set for each patient or for each doctor.

4. The medical image processing apparatus according to claim 2,
wherein in a case where the correspondence is changed, the storage stores the changed correspondence.

5. The medical image processing apparatus according to claim 1,
wherein the display control unit arranges the plurality of medical images in order of the degree of malignancy.

6. The medical image processing apparatus according to claim 1,
wherein the display control unit emphasizes or suppresses display of at least some medical images among the plurality of medical images by adding an emphasis flag to the medical image, adding a character to the medical image, adjusting a display color of the medical image, or adjusting a display size of the medical image.

7. The medical image processing apparatus according to claim 1,
wherein the processor further configured to function as a same abnormal region determination unit that determines whether or not the plurality of medical images each have the abnormal region including the same abnormality, and
wherein in a case where there are two or more medical images each having the abnormal region including the same abnormality, the display control unit emphasizes or suppresses display of at least some medical images among the two or more medical images each having the abnormal region including the same abnormality by using the degree of malignancy and an imaging distance of the medical image.

8. The medical image processing apparatus according to claim 7,
wherein the display control unit emphasizes or suppresses display of the medical image having a relatively short imaging distance, among the two or more medical images each having the abnormal region including the same abnormality.

9. The medical image processing apparatus according to claim 7,
wherein the display control unit emphasizes or suppresses display of the medical image having a relatively long imaging distance, among the two or more medical images each having the abnormal region including the same abnormality.

10. The medical image processing apparatus according to claim 7,
wherein the display control unit emphasizes or suppresses display of the medical image of which the imaging distance is close to a predetermined imaging distance determined for each imaging region in comparison with display of the other medical images, among the two or more medical images each having the abnormal region including the same abnormality.

11. The medical image processing apparatus according to claim 7,
wherein the display control unit preferentially emphasizes display of one or the plurality of medical images of which the imaging distance is relatively close to a reference imaging distance that differs depending on a procedure or suppresses display of one or the plurality of medical images of which the imaging distance is relatively far from the reference imaging distance, among the plurality of medical images.

* * * * *